(12) United States Patent
Dair et al.

(10) Patent No.: US 7,173,745 B2
(45) Date of Patent: Feb. 6, 2007

(54) OPTICAL BEAM DELIVERY CONFIGURATION

(75) Inventors: Geoffrey Thomas Dair, Subiaco (AU); Fred Norbert Reinholz, Floreat (AU)

(73) Assignee: Q-VIS Limited (AU)

( * ) Notice: Subject to any disclaimer, the term of this patent is extended or adjusted under 35 U.S.C. 154(b) by 173 days.

(21) Appl. No.: 10/476,323

(22) PCT Filed: Apr. 29, 2002

(86) PCT No.: PCT/AU02/00522

§ 371 (c)(1),
(2), (4) Date: Feb. 15, 2005

(87) PCT Pub. No.: WO02/088823

PCT Pub. Date: Nov. 7, 2002

(65) Prior Publication Data

US 2005/0146783 A1 Jul. 7, 2005

(30) Foreign Application Priority Data

Apr. 27, 2001 (AU) .................................. PR 4632

(51) Int. Cl.
*G02B 26/08* (2006.01)
*A61B 18/18* (2006.01)

(52) U.S. Cl. ..................... 359/196; 359/210; 359/676; 606/5

(58) Field of Classification Search ..................... None
See application file for complete search history.

(56) References Cited

U.S. PATENT DOCUMENTS

| | | | | |
|---|---|---|---|---|
| 4,353,617 A | * | 10/1982 | Tokumitsu et al. | 359/221 |
| 4,665,913 A | * | 5/1987 | L'Esperance, Jr. | 606/3 |
| 5,423,801 A | * | 6/1995 | Marshall et al. | 606/5 |
| 5,469,290 A | | 11/1995 | Maeda | |
| 5,558,666 A | * | 9/1996 | Dewey et al. | 606/9 |
| 5,980,513 A | * | 11/1999 | Frey et al. | 606/10 |

FOREIGN PATENT DOCUMENTS

| | | |
|---|---|---|
| EP | 715197 A | 6/1996 |
| JP | 2000-227564 A | 8/2000 |
| WO | WO 98/57604 | 12/1998 |

\* cited by examiner

Primary Examiner—James Phan
(74) Attorney, Agent, or Firm—Merchant & Gould P.C.

(57) ABSTRACT

An optical beam delivery configuration includes zoom lens means (30) and beam scanning means (44) defining an optical path (20) for a light beam. The beam scanning means is disposed after the zoom lens means in the direction of beam delivery. The zoom lens means (30) is arranged to receive a collimated incident light beam (23) on the optical path, and to be adjustable to determine the fluence of the beam when it is incident on the beam scanning means, while maintaining its collimation on exit from the zoom lens means. The beam scanning means (44) is arranged to laterally scan the beam at a downstream treatment location (50) while maintaining the beam's collimation and orientation at the location.

11 Claims, 2 Drawing Sheets

Object Plane                                    Image Plane

OPTICAL BEAM DELIVERY CONFIGURATION

FIELD OF THE INVENTION

This invention related generally to an optical beam delivery configuration, and has particular, though certainly not exclusive, application to the delivery of laser beams in medical laser systems. Such systems are used, for example, in a variety of ophthalmic surgical laser treatments such as the correction of refractive errors by reshaping the corneal stroma in PRK (photorefractive keratectomy) and LASIK (laser in-situ keratomileusis), the sealing of leaky retinal blood vessels, and the removal of debris from the posterior capsule of the lens after cataract surgery. The invention is also particularly applicable for any application that requires UV etching.

BACKGROUND ART

A fundamental requirement for beam delivery configurations in medical laser systems is an accurately predictable beam profile at the treatment site, eg. an anterior or internal corneal treatment surface. Known delivery systems generally include, among other components, a beam shaping means, typically defining an aperture that sets the beam cross-section, a scanner, and a fluence control. The latter is set to control fluence—energy density at a cross-section—to a fixed figure or at least below a predetermined limit for a given instrument and/or procedure. Such limits are usually predetermined by regulatory authorities and adherence to them is generally a mandatory condition of marketing approval by such authorities.

International patent publication WO 98/57604 discloses a laser beam delivery procedure and configuration in which the beam cross-section is varied during scanning, typically by being progressively increased as the surface being ablated is scanned in a predetermined pattern. Suitable scanning apparatus for this purpose is described in international patent publication WO 98/04303: that system has the particular benefit of maintaining the beam collimated and parallel to a fixed direction as it is laterally scanned. However, perfect collimation is often disturbed by at least two effects. Firstly, there is the disturbance arising from fluence control downstream of the scanner. Secondly, many laser device beam outputs are significantly variable in their cross-section and energy profile, and this causes still further variations at the fluence control as the latter in turn compensates for beam fluctuations.

The overall result of these imperfections is that, while a laser bream delivery system may incorporate a scanner arrangement in which the beam theoretically remains optically collimated as it is scanned, the system is still essentially height or z-axis sensitive, ie. the actual beam cross-section is dependent to some degree on the exact location of the treatment surface on the optical path or axis. In consequence, a predictable outcome of the procedure is dependent on having the treatment surface at an accurate location and on taking steps to prevent z-axis movement of the surface during the procedure. This adds to the complexity and sensitivity of typical ophthalmic laser surgery treatments: it would be preferable to provide an optical beam delivery system in which height or z-axis sensitivity was reduced, while making allowance for the reality of beam fluctuations in laser device outputs.

SUMMARY OF THE INVENTION

The invention provides, in one aspect, an optical beam delivery configuration including:

zoom lens means and beam scanning means defining an optical path for a light beam, said beam scanning means being disposed after said zoom lens means in the direction of beam delivery;

wherein said zoom lens means is arranged to receive a collimated incident light beam on said optical path, and to be adjustable to determine the fluence of the beam when it is incident on the beam scanning means, while maintaining its collimation on exit from the zoom lens means; and wherein said beam scanning means is arranged to laterally scan the beam at a downstream treatment location while maintaining the beam's collimation and orientation at the location.

Preferably, the configuration further includes beam shaping means in said optical path for determining the cross-sectional shape, perpendicular to the optical path, of said light beam. The beam shaping means is preferably disposed between the zoom lens means and the beam scanning means, and may typically comprise a variable aperture such as a variable iris for varying the beam-diameter.

The zoom lens means is preferably a three lens system including a first lens and, downstream thereof, a pair of lenses being a converging lens and a diverging lens respectively, which pair of lenses are arranged to move along the optical path relative to the first lens, with a fixed spatial relationship between the lenses of the pair, for determining the fluence of the beam.

To reduce or minimise the effect of back reflections in the zoom lens means, said pair of lenses are preferably a piano-convex lens and a concavo-plano lens, the former being upstream of the other relative to the direction of the beam.

The beam scanning means may substantially be as described in the aforementioned international patent publication WO 98/57604. Alternatively, the beam scanning means may include one or more converging or convex lenses selected and positioned having regard to their focal lengths so that one or more lenses may be translated laterally to effect scanning while maintaining the beam's collimation and orientation at the treatment location.

BRIEF DESCRIPTION OF THE DRAWINGS

The invention will be further described, by way of example only, with reference to the accompanying drawings, in which.

EMBODIMENTS OF THE INVENTION

Figure 1:
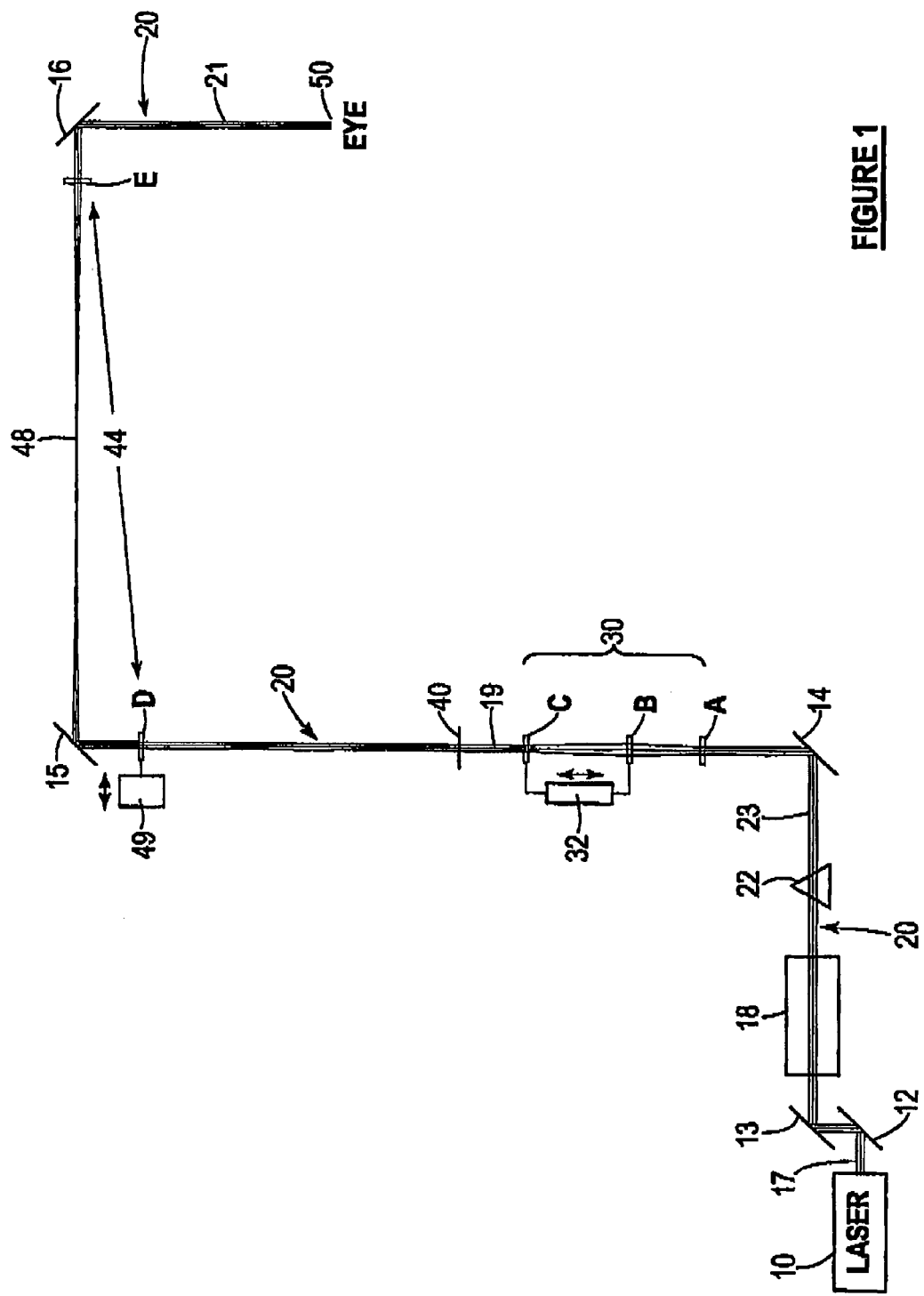
FIG. 1 is a schematic representation of a laser beam delivery configuration according to an embodiment of the invention.

FIG. 1 is an optical ray diagram for a laser beam delivery configuration according to an embodiment of the invention. The optical delivery is for a laser vision correction system and, although generally schematic and highly simplified, depicts correctly the relative locations of the components along the optical path.

The system is particularly suited for delivering a pulsed laser beam from a solid state laser such as an Nd:YAG laser 10 along an optical path 20 to a treatment location, in this case the cornea of an eye 50 of a patient, who would typically be lying on an adjacent bed. Path 20 includes segments in a post or other structure adjacent the bad and in an overhead cantilevered arm from which the beam is directed downwardly at 21 to the eye. The changes of direction in the path are defined by a series of mirrors 12, 13, 14, 15, 16 but it is emphasised that the actual folding and direction of the optical path may be quite different from that illustrated according to the overall structural layout of the installation. The diagram shows only certain optical components of relevance to the present invention: the system will include many other elements that are normally to be found in this kind of equipment, eg. a surgical microscope for viewing the procedure, a fixation device for holding the patients gaze, and optics for detecting and responding to movement of the eye on which the operation is being performed.

A typical procedure carried out with the illustrated system is vision correction by selectively and controllably reshaping a corneal surface by photoablation of tissue. A particularly suitable wavelength for this purpose is 213 nm. To obtain this wavelength, the 1064 nm primary or output beam 17 of laser 10 is passed through a sequence of non-linear optical crystals 18 to derive several harmonics, including the fifth harmonic wavelength 213 nm, of the fundamental wavelength 1064 nm. This fifth harmonic is separated from the others by a dispersing prism 22 to form a collimated 213 nm laser beam 23 on optical path 20.

Beam 23 is passed in turn in its direction of delivery through a fluence control in the form of a three-lens zoom telescope 30, beam shaping means in the form of an adjustable iris 40 and a scanner 44 formed by a pair of confocal lenses D, E. Scanner unit 44 also has an iris imaging capability with respect to iris 40, as will be explained subsequently.

Variable iris 40 determines the cross-sectional shape and diameter of beam 23 and of the beam actually delivered to the eye and, during a procedure, may typically be varied as the beam is scanned. Normally, iris 40 and scanner 44 are cooperatively controlled by a predetermined program to place pulses onto the corneal surface in order to produce a specific refractive outcome.

Figure 2:
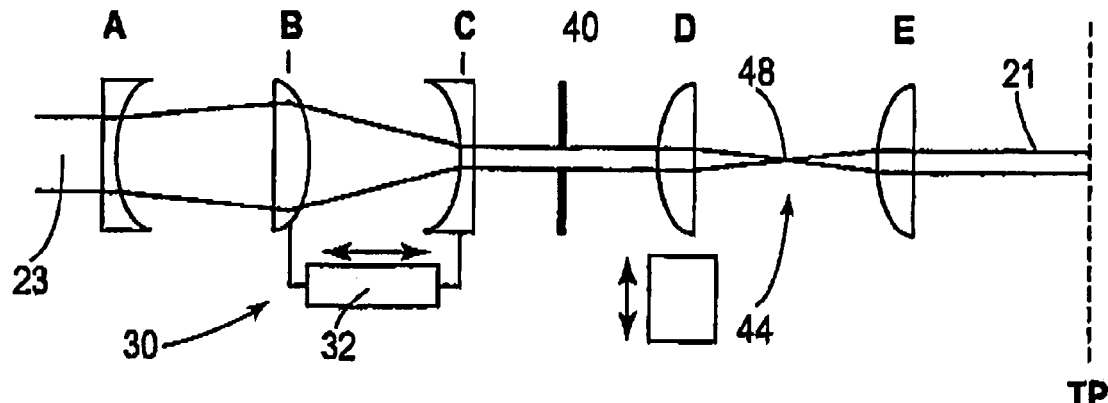
FIG. 2 is a not-to-scale diagram of the principal components of part of FIG. 1.

The form and arrangement of the fluence control 30 and scanner 44 are detailed in FIG. 2, which is a not-to-scale optical ray diagram of these components of the beam delivery system. Zoom telescope 30 has, in sequence along the optical path 20, a plano-concave lens A, a piano-convex lens B and a concave-plano lens C. The telescope works by providing lenses B, C with movement along the optical path to alter the beam magnification, thus varying the fluence. Lenses B, C are moved by translation unit 32, and must move with a fixed spatial relationship to maintain the beam collimation of the output 19 from lens C. This type of movement may be achieved with a CAM system, a direct drive or a linear drive as translation unit 32, and also allows any value of magnification to be obtained within the prescribed range. The illustrated three-lens telescope is a development in principle of the classical two-lens Galilean telescope, in which the focal lengths of the negative and positive lenses must coincide spatially and the magnification of the system is given by the ratio of the focal lengths of the two lenses. In the depicted arrangement, the lenses A and B can be viewed as forming a single lens of variable power. That is, as lens B is moved, the focal length of, the equivalent lens AB is altered. Therefore, in order to maintain the condition of coincident focal points, the third lens C must also be moved in unison with lens B.

It has been found preferable that lenses B and C be as shown rather than the converse, convex-piano and piano-convex concave respectively. With this latter arrangement, back reflections on lenses B, C are focussed back to lenses A, B respectively, risking an intense damaging spot on the upstream lens.

Scanner 44 comprises a pair of convex lenses D, E in the form of a Keplerian telescope, ie. the two lenses have coinciding focal points at an intervening point 48. If the two lenses have equal focal lengths, the beam diameter is unchanged at the output but it is preferred that a magnification factor 4:3 is produced so that the final lens E is the only lens in the sequence A to E which is exposed to the full fluence. It has been found that the typical fluence employed, 170 mJ/cm$^2$ can reduce the life of the optical components so there is advantage in reducing the fluence exposure at lenses C, D to 9/16 of the final fluence.

Beam scanning is achieved by off-axis translation, by translation unit 49, of lens D, resulting in a lateral movement of the beam at the treatment surface, indicated in FIG. 2 as a treatment plane TP. While this type of scanning does not distort the beam through the introduction of aberrations, the position of TP becomes critical in terms of the amount of lateral movement. It may be preferable to scan both lenses D and E in unison, which would provide lateral movement to parallel paths.

Figure 3:
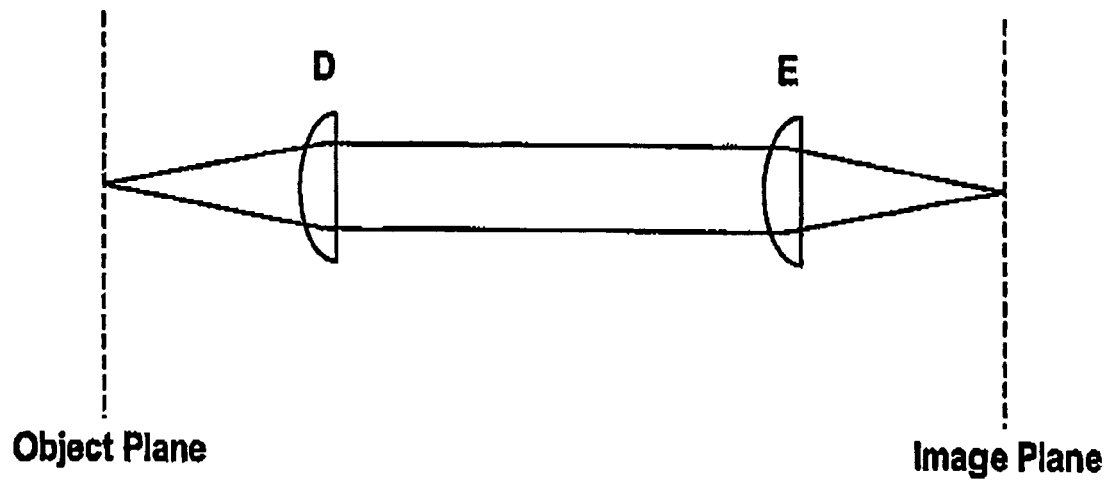
FIG. 3 is a simple optical ray diagram depicting the imaging properties of the lenses D, E shown in FIGS. 1 and 2.

Scanner 44 also possesses the potential for iris imaging, as illustrated diagrammatically in FIG. 3. An object placed in the front focal plane of lens D will be imaged in the back focal plane of lens E. Accordingly, the position of TP can be chosen to be in the imaging plane and the iris placed in the object plane. This has the disadvantage, however, of governing the position of TP.

By the particular sequence of fluence control and scanner, and with the iris preferably interposed between, the beam produced at the eye is reliably collimated and of predictable cross-section and fluence notwithstanding the variations in the laser beam, thus substantially eliminating height sensitivity. Moreover, this configuration is achieved with relatively few optical components in a simple layout.

The invention claimed is:

1. An optical beam delivery configuration including:
   zoom lens means and beam scanning means defining an optical path for a light beam, said beam scanning means being disposed after said zoom lens means in the direction of beam delivery;
   wherein said zoom lens mean is arranged to receive a collimated incident light beam on said optical path, and to be adjustable to determine the fluence of the beam when it is incident on the beam scanning means, while maintaining its collimation on exit from the zoom lens means; and
   wherein said beam scanning means is arranged to laterally scan the beam at a downstream treatment location while maintaining the beam's collimation and orientation at the location.

2. An optical beam delivery configuration according to claim 1 further including a beam shaping means in said optical path for determining the cross-sectional shape of said light beam perpendicular to said optical path.

3. An optical beam delivery configuration according to claim 2 wherein said beam shaping means is disposed in said optical path between said zoom lens means and said beam scanning means.

4. An optical beam delivery configuration according to claim 2 wherein said beam shaping means comprises a variable aperture for varying the beam diameter.

5. An optical beam delivery configuration according to claim 1 wherein said zoon lens means is a three lens system including a first lens and, downstream thereof in said direction of beam delivery, a pair of lenses being a converging lens and a diverging lens respectively, which pair of lenses is arranged to move along the optical path relative to the first lens, with a fixed spatial relationship between the lenses of the pair, for determining fluence of the beam.

6. An optical beam delivery configuration according to claim 5 wherein said lenses of said pair are a plano-convex lens and a concavo-plano lens, the plano-convex lens being upstream of the concavo-plano lens relative to said direction of beam delivery.

7. An optical beam delivery configuration according to claim 1 wherein said beam scanning means includes one or more converging or convex lenses selected and positioned having regard to their focal lengths so that one or more lenses may be translated laterally to effect scanning while maintaining the beam's collimation and orientation at the treatment location.

8. An optical beam delivery configuration according to claim 1, for receiving a primary laser beam generated by a solid state laser and further including a sequence of non-linear optical crystals for deriving a harmonic of said primary laser beam as said light beam delivered via said zoom lens means and said beam scanning means.

9. An optical beam delivery configuration according to claim 8 further including a solid state laser for generating said primary laser beam.

10. An optical beam delivery configuration according to claim 1, in ophthalmic surgical laser apparatus.

11. An optical beam delivery configuration according to claim 10 wherein said ophthalmic surgical laser apparatus is adapted for correction of refractive errors of the eye by reshaping of a corneal surface by photoablation of tissue.

* * * * *